US011813108B2

(12) United States Patent
Zucker et al.

(10) Patent No.: US 11,813,108 B2
(45) Date of Patent: Nov. 14, 2023

(54) SYSTEM AND METHOD OF GUIDANCE INPUT DETECTION AND SURGICAL EQUIPMENT POSITIONING

(71) Applicant: Mazor Robotics Ltd., Caesarea (IL)

(72) Inventors: Ido Zucker, Tel Aviv (IL); Avi Turgeman, Beer Yaakov (IL); Yonatan Ushpizin, Glil Yam (IL); Eli Zehavi, Tel Aviv (IL); Eitan Detinis, Shefayim (IL)

(73) Assignee: Mazor Robotics Ltd., Caesarea (IL)

( * ) Notice: Subject to any disclaimer, the term of this patent is extended or adjusted under 35 U.S.C. 154(b) by 100 days.

(21) Appl. No.: 17/353,342

(22) Filed: Jun. 21, 2021

(65) Prior Publication Data
US 2022/0401056 A1 Dec. 22, 2022

(51) Int. Cl.
*A61B 6/00* (2006.01)
*A61B 6/06* (2006.01)
*A61B 90/00* (2016.01)

(52) U.S. Cl.
CPC .............. *A61B 6/548* (2013.01); *A61B 6/06* (2013.01); *A61B 6/4452* (2013.01); *A61B 6/4458* (2013.01); *A61B 2090/064* (2016.02)

(58) Field of Classification Search
CPC ... A61B 2090/064; A61B 6/06; A61B 6/4429; A61B 6/4452; A61B 6/4458; A61B 6/4476; A61B 6/547; A61B 6/548
See application file for complete search history.

(56) References Cited

U.S. PATENT DOCUMENTS

| | | | |
|---|---|---|---|
| 9,867,588 | B2 | 1/2018 | Amiri |
| 2017/0209217 | A1* | 7/2017 | Jensen ................. A61B 6/4458 |
| 2019/0125460 | A1 | 5/2019 | Maillet et al. |
| 2020/0121267 | A1 | 4/2020 | Deutschmann |
| 2021/0093333 | A1 | 4/2021 | Chappuis et al. |

OTHER PUBLICATIONS

International Search Report for International (PCT) Patent Application No. PCT/IL2022/050653, dated Oct. 11, 2022, 10 pages.

* cited by examiner

*Primary Examiner* — Dani Fox
(74) *Attorney, Agent, or Firm* — Sheridan Ross P.C.

(57) ABSTRACT

A system according to at least one embodiment of the present disclosure includes an imaging source; an imaging detector; a sensor coupled to at least one of the imaging source and imaging detector; and a controller that adjusts a relative position of the imaging source and the imaging detector based on an output of the sensor.

20 Claims, 10 Drawing Sheets

SYSTEM AND METHOD OF GUIDANCE INPUT DETECTION AND SURGICAL EQUIPMENT POSITIONING

FIELD

The present technology generally relates to surgical procedures, and more particularly to adjusting imaging equipment to assist with surgical procedures.

BACKGROUND

Surgical robots may assist a surgeon or other medical provider in carrying out a surgical procedure or may complete one or more surgical procedures autonomously. Imaging may be used by a medical provider for diagnostic and/or therapeutic purposes. Imaging may be used to capture one or more elements of patient anatomy while carrying out a surgery or surgical procedure. The imaging equipment may use X-rays to generate images of the patient anatomy.

SUMMARY

Example aspects of the present disclosure include:

A system according to at least one embodiment of the present disclosure comprises: an imaging source; an imaging detector; a sensor coupled to at least one of the imaging source and imaging detector; and a controller that adjusts a relative position of the imaging source and the imaging detector based on an output of the sensor.

Any of the aspects herein, wherein the sensor comprises a force sensor.

Any of the aspects herein, wherein the imaging source is moved with a first robotic arm, and wherein the imaging detector is moved with a second robotic arm.

Any of the aspects herein, wherein the controller adjusts at least one of the imaging source and the imaging detector using an electromechanical linkage, and wherein the electromechanical linkage comprises an O-arm, a C-arm, or a G-arm.

Any of the aspects herein, wherein the controller adjusts the relative position of the imaging source and the imaging detector such that the imaging source is substantially aligned with the imaging detector.

Any of the aspects herein, wherein the imaging source is spaced a first distance from the imaging detector in a first orientation, wherein the imaging source is spaced a second distance from the imaging detector in a second orientation different from the first orientation.

Any of the aspects herein, wherein the first distance is greater than the second distance.

Any of the aspects herein, wherein the first distance is less than the second distance.

Any of the aspects herein, further comprising: a collimator operatively coupled with at least one of the imaging source and the imaging detector, wherein the controller adjusts a position of the collimator based on the output of the sensor.

Any of the aspects herein, wherein the controller adjusts the position of the collimator such that the collimator is aligned with the imaging source along a first axis.

A system in accordance with at least one embodiment of the present disclosure comprises: a first robotic arm; a sensor operatively coupled with the first robotic arm; and a controller that receives a first input from the sensor related to the movement of the first robotic arm, wherein the controller causes a second robotic arm to move relative to the first robotic arm.

Any of the aspects herein, wherein the sensor comprises a force sensor.

Any of the aspects herein, wherein the second robotic arm is positioned a first distance from the first robotic arm at a first time, wherein the second robotic arm is a second distance from the first robotic arm at a second time, and wherein the first distance is different from the second distance.

Any of the aspects herein, further comprising: a locking mechanism that switches one or more of the first robotic arm and the second robotic arm between a locked state and an unlocked state, wherein, when in the locked state, the first robotic arm and the second robotic arm are prevented from being moved, and wherein, when in the unlocked state, the first robotic arm and the second robotic arm are configured to be moved.

Any of the aspects herein, wherein the locking mechanism comprises at least one of a floor pedal, a button, and a lever.

Any of the aspects herein, further comprising: an imaging source connected to the first robotic arm; an imaging detector connected to the second robotic arm; and a collimator operatively connected to at least one of the imaging source and the imaging detector and configured to be adjusted based on the output of the sensor.

Any of the aspects herein, wherein the collimator is in a first orientation at a first time, and wherein, at a second time, the controller moves the collimator into a second orientation.

Any of the aspects herein, wherein the collimator is substantially aligned with the imaging source in at least one of the first orientation and the second orientation.

A system in accordance with at least one embodiment of the present disclosure comprises: a processor; and a memory storing data for processing by the processor that, when processed by the processor, cause the processor to: receive an input from at least one sensor, the input related to a movement of a first robotic arm; and output a control signal, the control signal causing a second robotic arm to move relative to the first robotic arm.

Any of the aspects herein, wherein the second robotic arm moves substantially synchronously with the first robotic arm.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1-X_n$, $Y_1-Y_m$, and $Z_1-Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
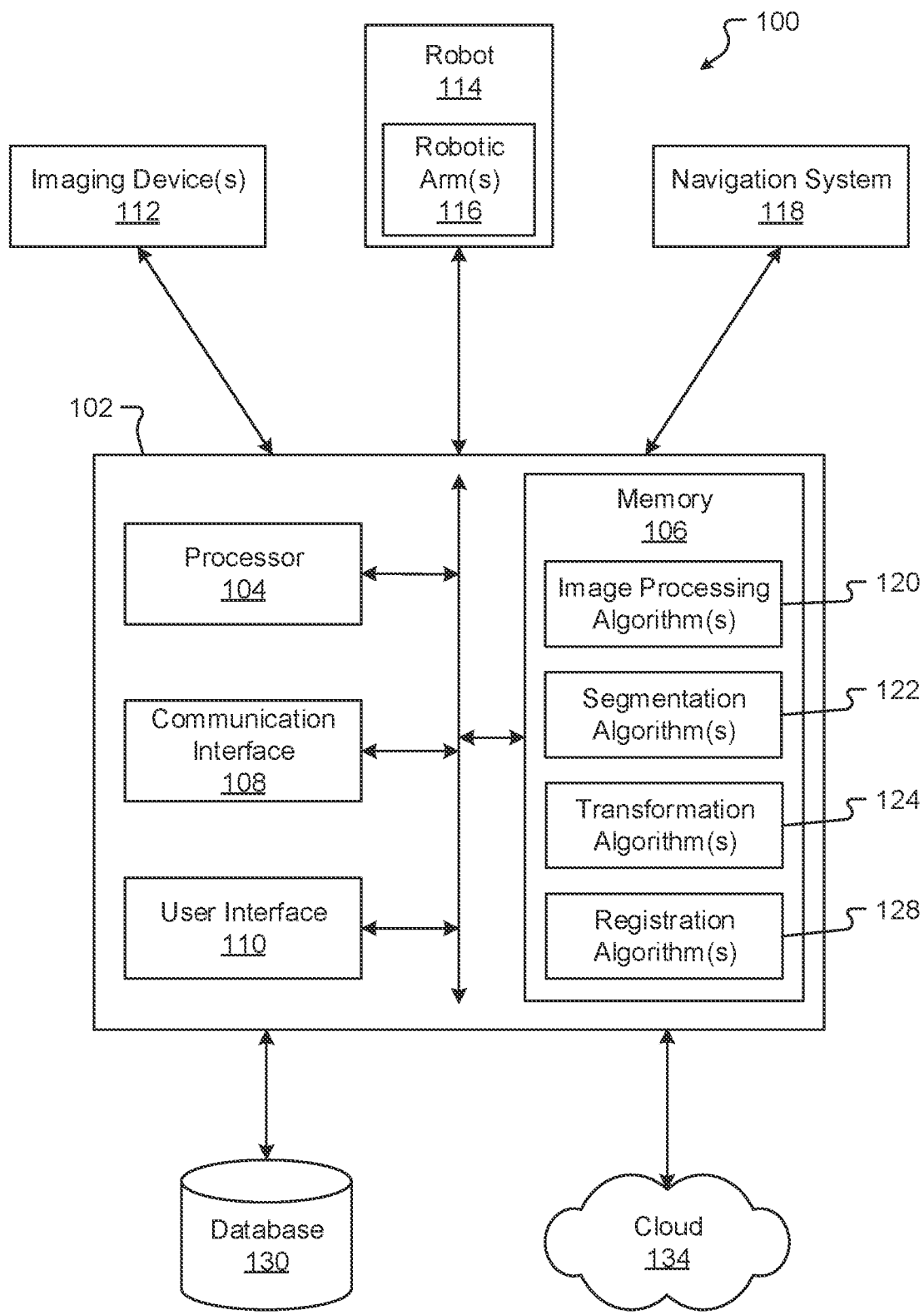
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

During orthopedic surgery, the medical staff may use imaging techniques to view patient anatomy and/or a Region of Interest (ROI). Embodiments of the present disclosure may utilize imaging components may include rigid apparatuses (e.g., a C-arm) or may be multiple robotic arms configured to hold and move the imaging components (i.e., an imaging detector and an imaging source).

In at least one embodiment of the present disclosure, a robotic configuration is used, where a first robotic arm holds an imaging detector (i.e., the device that receives the X-ray) and a second robotic arm holds an imaging source (i.e., the device that generates the X-ray). In order to facilitate generation of an image, the first and second robotic arms should perform synchronized movement relative to one another, such that the imaging source and the imaging detector are aligned.

Embodiments of the present disclosure permit a user (e.g., a surgeon or other medical technician or professional) to guide one of the robotic arms (which may be connected to the imaging source), with the other robotic arm (which may be connected to the imaging detector) moving synchronously and complementarily, such that the imaging is enabled after the movement of the robotic arms. For example, after the first robotic arm is moved (e.g., by the user), the orientation of the second robotic arm may be changed (e.g., the distance between the two robotic arms changes, the second robotic arm spins about a main axis, etc.) such that the imaging source and imaging detector are aligned.

Embodiments of the present disclosure may additionally attach a collimator (e.g., a collimator with 3 degrees of freedom) to one of the robotic arms. The movement of the first robotic arm by the user may also cause the orientation of the collimator to change such that the imaging source and the imaging detector are aligned and capable of generating images.

Embodiments of the present disclosure provide technical solutions to one or more of the problems of (1) errors in the positioning of imaging components, and (2) limitations on surgeon positioning of imaging components relative to patient anatomy.

Turning first to FIG. 1, a block diagram of a system 100 according to at least one embodiment of the present disclosure is shown. The system 100 may be used to position imaging components relative to patient anatomy and/or an ROI; capture images of the patient anatomy and/or the RIO; and/or carry out one or more other aspects of one or more of the methods disclosed herein. The system 100 is illustrated to include a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400 and/or 500 described herein, or of any other methods. The memory 106 may store, for example, one or more image processing algorithms 120, one or more segmentation algorithms 122, one or more transformation algorithms 124, and/or one or more registration algorithms 128. Such instructions or algorithms may, in some embodiments, be organized into one or more applications, modules, packages, layers, or engines. Alternatively or additionally, the memory 106 may store other types of data (e.g., machine learning modes, artificial neural networks, etc.) that can be processed by the processor 104 to carry out the various method and features described herein. Thus, although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors (such as one or more sensors 240 described in greater detail below) that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The system 100 or similar systems may be used, for example, to carry out one or more aspects of any of the methods 400 and/or 500 described herein. The system 100 or similar systems may also be used for other purposes.

Figure 2:
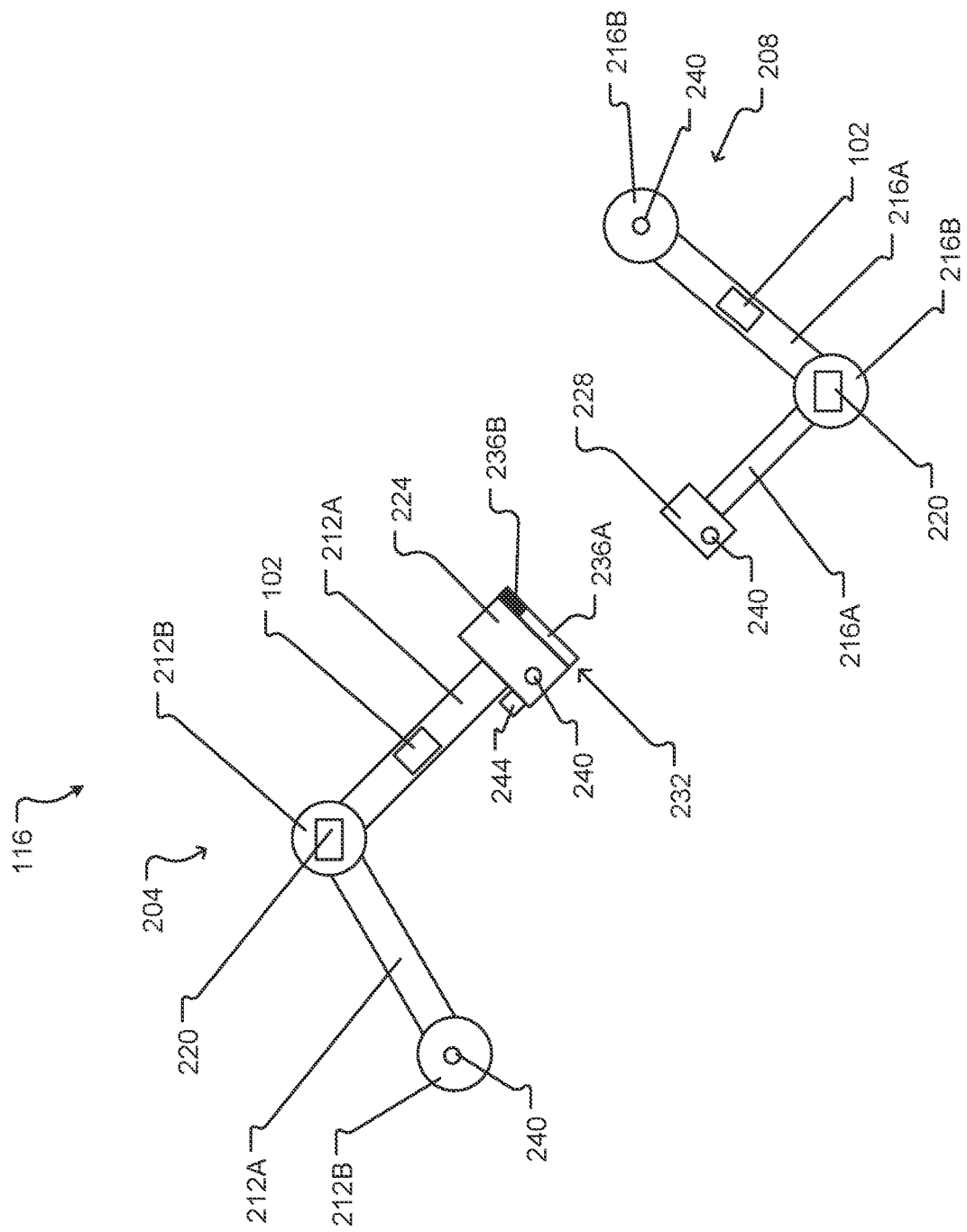
FIG. 2 is a schematic view of robotic arms according to at least one embodiment of the present disclosure.

Turning to FIG. 2, a schematic view of robotic arms 116 is shown in accordance with at least one embodiment of the present disclosure. The robotic arms 116 depicted in FIG. 2 may include a first robotic arm 204 (which may comprise one or more members 212A connected by one or more joints 212B) and a second robotic arm 208 (which may comprise one or more members 216A connected by one or more joints 216B). In some embodiments, the robotic arms 116 may comprise additional robotic arms (e.g., a robotic arm for holding and/or maneuvering a surgical tool). The first robotic arm 204 and the second robotic arm 208 may operate in a shared or common coordinate space. By operating in the common coordinate space, the first robotic arm 204 and the second robotic arm 208 in the common coordinate space, the first robotic arm 204 and the second robotic arm 208 avoid colliding with each other during use, as a position of each of the robotic arms 204, 208 is known to each other. In other words, because each of the first robotic arm 204 and the second robotic arm 208 have a known position in the same common coordinate space, collision can be automatically avoided as a controller of the first robotic arm 204 and of the second robotic arm 208 is aware of a position of both of the robotic arms. In some embodiments, the first robotic arm 204 and/or the second robotic arm 208 may be registered to the patient.

Each of the first robotic arm 204 and the second robotic arm 208 may comprise one or more motors 220. The motors 220 may be positioned in one or more of the members 212A, 216A and/or the joints 212B, 216B and may cause the members 212A, 216 and/or the joints 212B, 216B to move such that the first robotic arm 204 moves relative to the second robotic arm 208, or vice versa. The motors 220 may be include a DC brushed motor, an AC or DC brushless motor, a servo motor, a stepper motor, a turbine motor, combinations thereof, or the like. In some embodiments, the motors may be wired or wireless connected to a computing device 102. The computing device 102 may send signals (e.g., via the wired or wireless connection) to actuate the motors 220 to cause the robotic arms 204, 208 to move. In some embodiments, the first robotic arm 204 and the second robotic arm 208 may be both controlled by a single computing device 102, with the single computing device 102 being disposed in the first robotic arm 204, the second robotic arm 208, or another component (e.g., a component of the system 100). In some embodiments, the second robotic arm 208 (or more specifically the motors 220 coupled thereto) may receive control signals from the computing device 102 based on a relative movement associated with the first robotic arm 204, or vice versa. For example, a user (e.g., a surgeon, an operating room technician, or the like) may cause the first robotic arm 204 to move, such as by pushing on the first robotic arm 204. The computing device 102 may receive, based on the push, sensor data generated by a sensor 240 coupled with the first robotic arm 204, and may send signals to the second robotic arm 208 to cause the second robotic arm 208 to move in a complementary direction.

The first robotic arm 204 may be connected to an imaging source 224 and the second robotic arm 208 may be connected to an imaging detector 228. The imaging source 224 generates or otherwise emits radiation, waves, or other signals that are received or captured by the imaging detector 228 to generate an image of the anatomical elements (e.g., patient anatomy) positioned therebetween. The robotic arms 116 may additionally comprise a collimator 232. The collimator 232 aligns the X-rays or other signals passing therethrough (e.g., X-rays generated by the imaging source 224, X-rays captured by the imaging detector 228, and so forth) to, for example, improve the resulting image. In some embodiments, the collimator 232 may comprise an open portion 236A and a closed portion 236B, with the open portion 236A permitting X-rays or other signals to pass therethrough, and the closed portion 236B preventing the X-rays or other signals to pass therethrough. In some embodiments, the collimator 232 may comprise an open portion 236A and a closed portion 236B. The open portion 236A may be or comprise a portion of the collimator 232 through which X-rays or other signals may pass, and through which the passing X-rays are focused or aligned. The closed portion 236B may be or comprise a portion of the collimator 232 through which X-rays or other signals are blocked or prevented from passing.

In some embodiments, the collimator 232 may comprise one, two, three, or more degrees of freedom. For instance, the collimator 232 may comprise three degrees of freedom, with the collimator capable of opening or closing one or more shutters in a first direction (e.g., an X-axis direction) and a second direction (e.g., a Y-axis direction), while also capable of rotating the shutters independently of one another such that an open portion of the collimator (i.e., the portion through which the X-rays are focused) is capable of rotating in a first plane (e.g., in the XY-plane). In some embodiments, the shutters may be controlled by the one or more motors 220. In some embodiments, the computing device 102 may determine the pose of the collimator and/or the shape and dimensions of the open portion 236A based on the movement of the first robotic arm 204 and the complementary movement of the second robotic arm 208 such that the emissions from the imaging source 224 are captured by the imaging detector 228. In some embodiments, the collimator 232 may be automatically adjusted (e.g., based on signals from the computing device 102) based on instructions processed by the computing device 102. In some embodiments, the collimator 232 may be attached to a third robotic arm (not shown), with the third robotic arm being pose-adjusted by the computing device 102 based on the movement of the first robotic arm 204 and/or the second robotic arm 208 to ensure alignment between the imaging source 224 and the imaging detector 228.

As previously mentioned, one or more sensors 240 may be disposed on, disposed in, and/or otherwise coupled to one or more of the first robotic arm 204 and the second robotic arm 208. The sensor 240 may be one or more devices that detect, sense, measure, and/or otherwise receive an input (e.g., a force input from the user pushing on the first robotic arm 204, a force input from the user pulling on the second robotic arm 208, etc.) that enables a processor 104 or the computing device 102 to determine a desired or required movement of the first robotic arm 204 and/or the second robotic arm 208 based on the input. For example, the sensor 240 may be or comprise a force sensor (e.g., a transducer that converts a mechanical input load into an electrical signal) and/or a vibrational sensor that, when the user presses on the sensor 240 or an area proximate thereto, may send information related to the magnitude and direction of the applied force to one or more components of the system 100 (e.g., to the computing device 102, to the processor 104, etc.). In some embodiments, the sensors 240 may be additionally or alternatively positioned on, within, or be coupled with the members 212A, 126A and/or the joints 212B, 216B.

The first robotic arm 204 and/or the second robotic arm 208 may comprise a button 244. The button 244 may, once pressed, send one or more signals that cause one or more actions within the system 100 (or components thereof). For instance, the button 244 may be electrically coupled to the imaging source 224 and/or the imaging detector 228 such that, upon activation of the button 244 (e.g., by the user), the imaging source 224 begins to emit. In some embodiments, the imaging source 224 may continue to emit until the button 244 is pressed again. In other embodiments, the imaging source 224 may only emit as long as the button 244 is pressed. In some embodiments, the button 244 may be communicatively connected to the computing device 102, and may, upon activation, send a signal to the computing device 102 to cause the movement of the first robotic arm 204 and/or the second robotic arm 208. In such embodiments, the computing device 102 may require both a force input measured at a sensor 240 and an activation of the button 244 before causing the first robotic arm 204 and/or the second robotic arm 208 to move.

FIGS. 3A-3F show various views of a robotic platform 300 according to at least one embodiment of the present disclosure. The platform 300 includes a support structure 304 and an operating table 324. The structure 304 comprises an upper wall or member 308, a lower wall or member 312, and a pair of sidewalls or members 316A, 316B. In some embodiments, the table 324 is positioned orthogonally to the support structure 304, such that the table 324 may extend in a first direction from the support structure 304. In some embodiments, the table 324 may be mounted to the support structure 304. In other embodiments, the table 324 may not be mounted to the support structure 304 and may be mounted elsewhere.

In some embodiments, the structure 304 is fixed securable to an operating room wall 320 (such as, for example, a ground surface of an operating room or other room). In other embodiments, the support structure 304 may be releasably securable to the operating room wall 320 or may be a standalone component that is simply supported by the operating room wall 320. In some embodiments, the table 324 may be mounted to the structure 304. In other embodiments, the table 324 may be releasably mounted to the structure 304. In still other embodiments, the table 324 may not be attached to the structure 304. In such embodiments, the table 324 may be supported and/or mounted to an operating room wall, for example. In embodiments where the table 324 is mounted to the structure 304 (whether detachably mounted or permanently mounted), the table 324 may be mounted to the structure 304 such that a pose of the table 324 relative to the structure 304 is selectively adjustable.

The table 324 may be any operating table 324 configured to support a patient during a surgical procedure. The table 324 may include any accessories mounted to or otherwise coupled to the table 324 such as, for example, a bed rail, a bed rail adaptor, an arm rest, an extender, or the like. The operating table 324 may be stationary or may be operable to maneuver a patient (e.g., the operating table 324 may be able to move). In some embodiments, the table 324 has two positioning degrees of freedom and one rotational degree of freedom, which allows positioning of the specific anatomy of the patient anywhere in space (within a volume defined by the limits of movement of the table 324). For example, the table 324 can slide forward and backward and from side to side, and can tilt (e.g., around an axis positioned between the head and foot of the table 324 and extending from one side of the table 324 to the other) and/or roll (e.g., around an axis positioned between the two sides of the table 324 and extending from the head of the table 324 to the foot thereof). In other embodiments, the table 324 can bend at one or more areas (which bending may be possible due to, for example, the use of a flexible surface for the table 324, or by physically separating one portion of the table 324 from another portion of the table 324 and moving the two portions independently). In at least some embodiments, the table 324 may be manually moved or manipulated by, for example, a surgeon or other user, or the table 324 may comprise one or more motors, actuators, and/or other mechanisms configured to enable movement and/or manipulation of the table 324 by a processor such as the processor 104.

The platform 200 also comprises a first robotic arm 204 and a second robotic arm 208. Both the first robotic arm 204 and the second robotic arm 208 may be dimensioned so that one or more of the robotic arms may reach various portions of a patient such as, for example, a patient spine. In some embodiments, the first robotic arm 204 and/or the second robotic arm 208 may be independent of and unattached from the table 324. In other words, the first robotic arm 204 and/or the second robotic arm 208 may be manipulated and moved separately from the table 324. In such embodiments, the plurality of robotic arms 216 may be secured to one or more of a floor, a wall, and/or ceiling of an operating room, or to any structure of the platform 300. In other embodiments, the first robotic arm 204 and/or the second robotic arm 208 may be attached directly to the table 324. In some embodiments, the first robotic arm 204 and/or the second robotic arm 208 may be attached to the table 324 with a gantry. In other embodiments, the first robotic arm 204 and/or the second robotic arm 208 may be attached to the table 324 without a gantry.

Figure 3A:
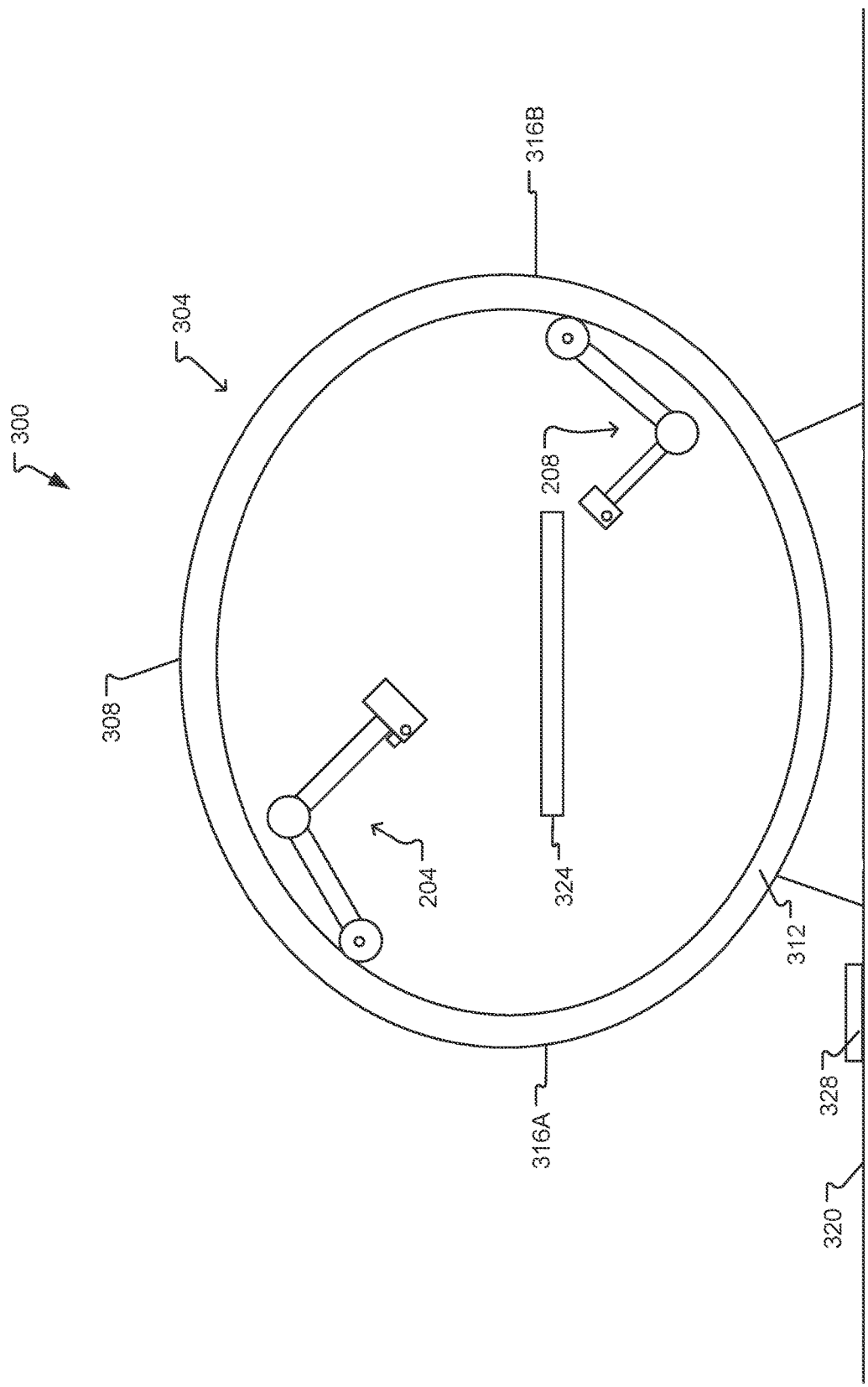
FIG. 3A is a first diagram of a robotic platform in according to at least one embodiment of the present disclosure.

In the embodiment illustrated in FIG. 3A, a first robotic arm 204 is attached to or otherwise mounted to the first sidewall 316A and a second robotic arm 208 is attached to or otherwise mounted to the second sidewall 316B. It will be appreciated that the platform 300 may have any number of robotic arms including one robotic arm, two robotic arms, or more than two robotic arms. In the illustrated embodiment, the first robotic arm 204 and the second robotic arm 208 are also shown positioned on opposite sides of the aperture 304. In other embodiments, the first robotic arm 204 and the second robotic arm 208 may be positioned anywhere along the aperture 304. In some embodiments, a third robotic arm (not shown) may be mounted to the lower wall 312 or the upper wall 308. In still further embodiments, any number of robotic arms 116 may be positioned anywhere on any component of the platform 300 or surgical room (e.g., on the table 324, the support structure 304, and/or an operating room wall 320).

As previously mentioned, the first robotic arm 204 and the second robotic arm 208 may be capable of or operable to manipulate an imaging source 224 and an imaging detector 228, respectively. In some instances, the first robotic arm 204 may orient the imaging source 224 and the second robotic arm 208 may orient the imaging detector 228 so as to provide between and including 0 to 360-degree imaging of a patient positioned on the table 324. In some embodiments, the imaging source 224 and the imaging detector 228 may provide between and including 0 to 360-degree imaging of a patient during, for example, a surgical task or procedure.

The first robotic arm 204 and the second robotic arm 208 may be coupled with or by an electromechanical linkage. The electromechanical linkage causes the second robotic arm 208 to be moved in response to a detected movement of the first robotic arm 204, or vice versa. In at least one embodiment, the electromechanical linkage comprises an O-arm, a C-arm, a G-arm, or any device capable of facilitating the movement of the first robotic arm 204 or the second robotic arm 208. Additionally or alternatively, the electromechanical linkage may comprise a controller or other computing device such as the computing device 102. The computing device 102 may be coupled with the first robotic arm 204 and/or the second robotic arm 208, with the computing device 102 receiving input related to a first movement (e.g., sensor data from the sensor 240 indicating the user has applied a force to the first robotic arm 204 to move the first robotic arm 204 from a first pose to a second pose), determining a corresponding pose for the second robotic arm 208 relative to the first robotic arm 204, and moving the second robotic arm 208 to the new pose.

In some embodiments, the computing device 102 may process instructions that cause the motors 220 to automatically position the first robotic arm 204 and/or the second robotic arm 208 based on the instructions. For example, a surgeon may require a scan of a patient's spine (e.g., images of each vertebra in the spine), and may apply a force to the first robotic arm 204 or the second robotic arm 208. The force may be detected by the sensor 240, which may send a signal to the computing device 102 indicating the user wishes to move the robotic arms 204, 208. The computing device 102 may process instructions (e.g., instructions from a memory 106, a database 130, a cloud 134, etc.) that cause the first robotic arm 204 (and subsequently the imaging source 224) to move to a first pose relative to the spine and cause the second robotic arm 208 to move to a complementary pose, such that the imaging detector 228 is substantially aligned with the imaging source 224. The instructions may then further cause the computing device to cause the first robotic arm 204 and the second robotic arm 208 to move such that the imaging source 224 and the imaging detector 228 move down part or the entirety of the patient's spine, align at each vertebra, and automatically capture an image of each of the vertebra. The instructions may be based on, for example, a type of surgery being performed (e.g., the instructions may cause the robotic arms to be positioned such that a spinal scan is captured based on a planned spinal surgery). In some embodiments, the computing device 102 may cause the second robotic arm 208 to move substantially synchronously with the first robotic arm 204.

As used herein, and unless otherwise specified, "substantially synchronously" means that the second robotic arm 208 and/or the collimator 232 is caused to move within one second of the movement of the first robotic arm 204, or vice versa. In other embodiments, "substantially synchronously" may mean that the second robotic arm 208 and/or the collimator 232 is caused to move within 500 milliseconds (ms), within 200 ms, within 100 ms, or within 50 ms of the movement of the first robotic arm 204, or vice versa.

As used herein, and unless otherwise specified, "substantially aligned" means that the imaging source and the imaging detector are positioned such that emitted particles from the imaging source are detected by the imaging detector, such that an image can be formed. In some embodiments, "substantially aligned" may mean axially aligned such that at least a portion of the emitted particles are detected by the imaging detector.

Unless otherwise specified, "complementary" as used herein to define the movement of one robotic arm relative to another robotic arm means that the second robotic arm that moves (e.g., the robotic arm not contacted or that does not receive an input force from the user) is caused to move in such a way that an imaging detector attached or otherwise connected to the second robotic arm is aligned with an imaging source attached or otherwise connected to the first robotic arm, such that an image can be created from the X-rays or other radiation emitted from the imaging source and captured by the imaging detector. In other embodiments, "complementary" may mean that a collimator is caused to move such that the X-rays or other radiation emitted from the imaging source is focused into the imaging detector.

Figure 3B:
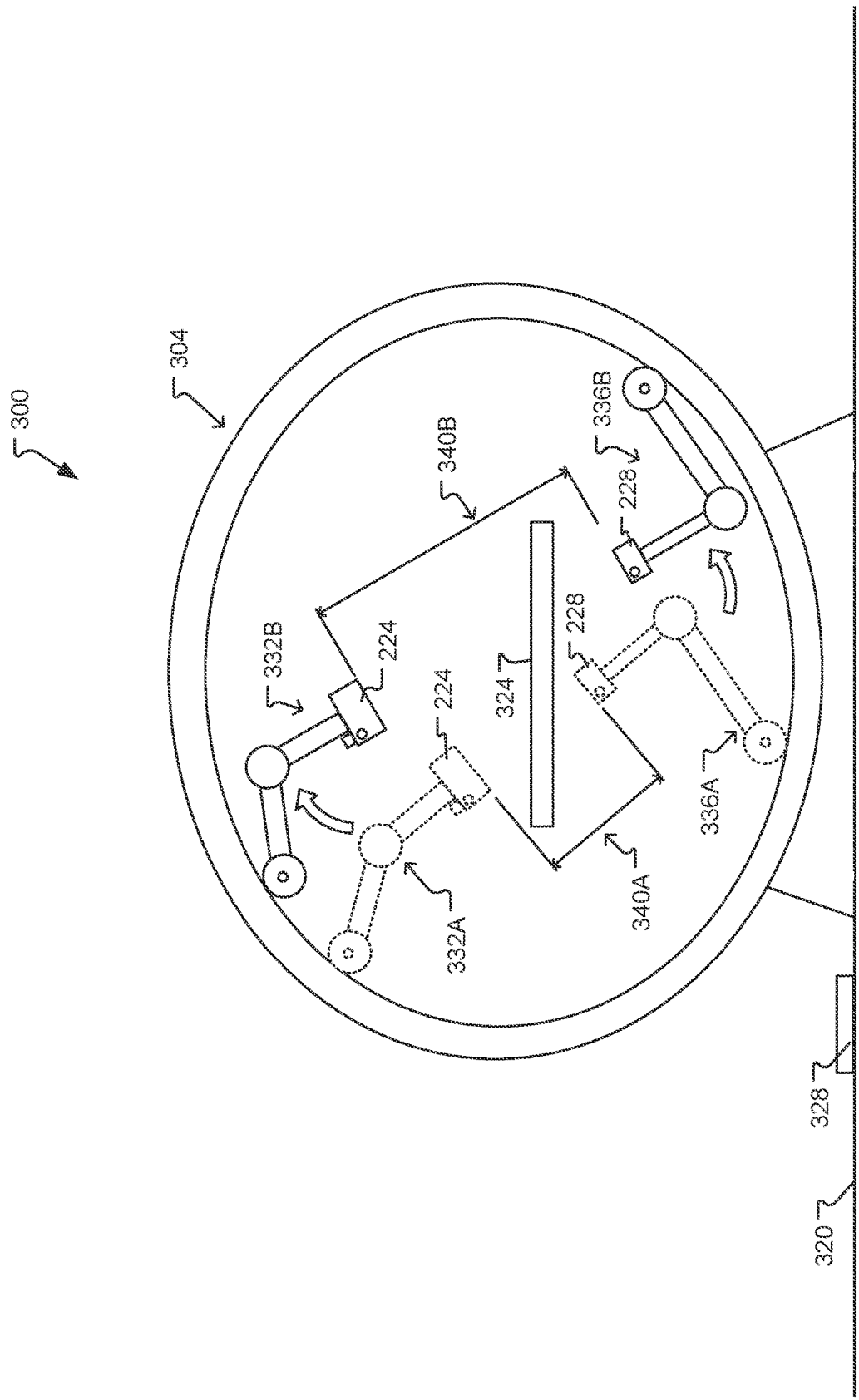
FIG. 3B is the first diagram of the robotic platform in a first orientation according to at least one embodiment of the present disclosure.

In the embodiment illustrated in FIG. 3B, the first robotic arm 204 is initially in a first pose 332A, and the second robotic arm 208 is in a first pose 336A such that the imaging source 224 and the imaging detector 228 are axially aligned, such that the signals emitted from the imaging source 224 are captured by the imaging detector 228 (which may allow for imaging of any anatomical elements positioned between the imaging source 224 and the imaging detector 228). The first robotic arm 204 is then moved to a second pose 332B.

The first robotic arm 204 may be moved when, for example, a user (e.g., a physician, an operating room technician, etc.) applies a force to the first robotic arm 204. The first robotic arm 204 may be moved based on the preference of the user, or for any other reason. For example, the surgeon may determine that the imaging source 224 is not positioned or aligned in a desired pose relative to the anatomical element being imaged (e.g., the imaging source 224 is not capturing the desired vertebra, the imaging source 224 is not capturing an image of the vertebra at the desired angle, etc.) or that improved imaging could be made with small adjustments to the pose of the imaging source 224. In the course of moving the robotic arm 204 and/or the imaging source 224, the user may apply a force thereto that is captured by the one or more sensors 240. The magnitude and direction of the applied force may be captured by the sensors 240, which may be transmitted to the computing device 102. The computing device 102 may receive the sensor data and may determine a complementary movement of the second robotic arm 208 and/or the imaging detector 228 such that the imaging detector 228 is aligned with the imaging source 224 once the first robotic arm 204 (and, by extension, the imaging source 224) is in the second pose 332B and may cause the robotic arm 208 and/or the imaging detector 228 to move in the complementary manner. The complementary movement of the second robotic arm 208 and/or the imaging detector 228 may be based on, but in no way limited to, the anatomical elements or objects being imaged, the type of surgery, the type of physician, combinations thereof, and/or the like.

In some embodiments, the first robotic arm 204 may be moved from the first pose 332A to the second pose 332B in order to expand the area exposed to the radiation (e.g., X-rays) emitted from the imaging source 224. For instance, in the first pose 332A, the imaging source 224 may be positioned a first distance 340A from the imaging detector 228, with the first distance 340A being too small (i.e., the imaging source 224 and the imaging detector 228 are too close) to capture images of a desired anatomical element (e.g., a vertebra). The movement of the first robotic arm 204 to the second pose 332B may result in a second distance 340B between the imaging source 224 and the imaging detector 228 greater than the first distance 340A, permitting a greater area of the patient to be exposed to X-rays emitted from the imaging source 224 in order to capture an image of the desired anatomical element. In some embodiments, the computing device 102 may cause the second robotic arm 208 to move such that the imaging detector 228 moves further away from the imaging source 224 to facilitate or improve the imaging of the desired anatomical element.

Figure 3C:
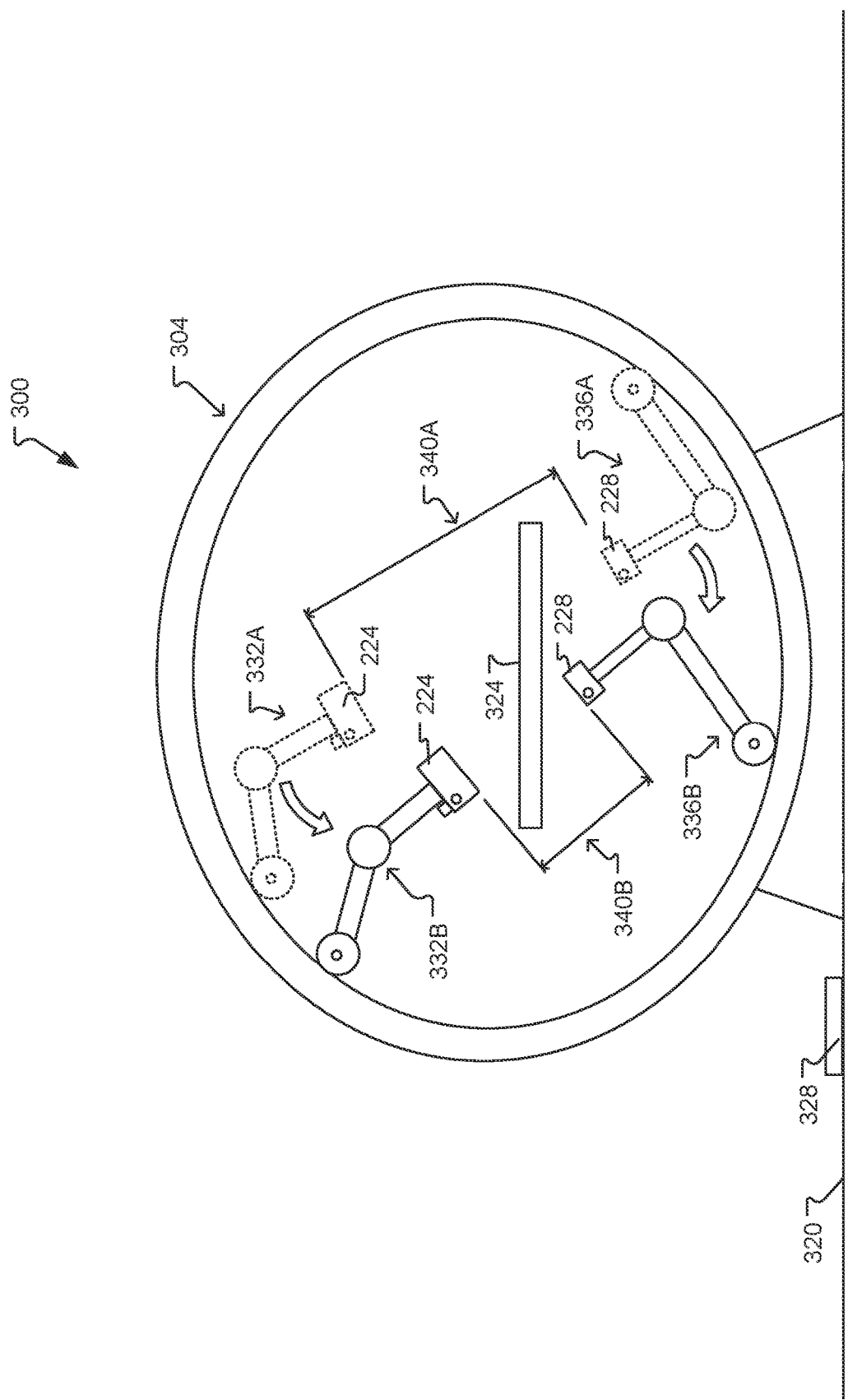
FIG. 3C is the first diagram of the robotic platform in a second orientation according to at least one embodiment of the present disclosure.
Figure 3D:
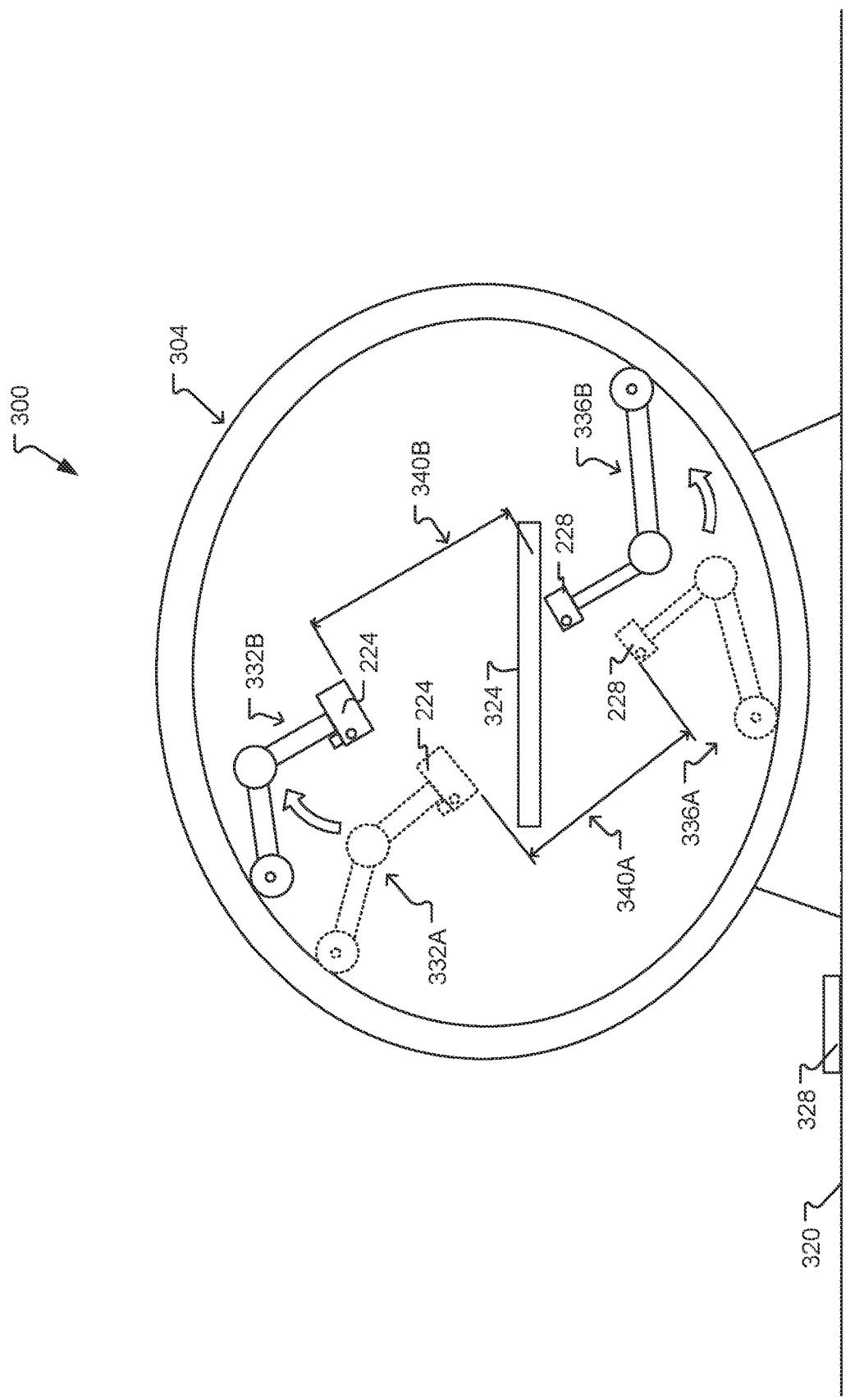
FIG. 3D is the first diagram of the robotic platform in a third orientation according to at least one embodiment of the present disclosure.

In some embodiments, such as the embodiment shown in FIG. 3C, the first robotic arm 204 may move from the first pose 332A to the second pose 332B, where the second pose 332B is closer to the table 324 (and subsequently the patient anatomy). In such embodiments, the user may determine that the X-rays should be more narrowly focused on an area of the patient (e.g., an individual vertebra rather than the entire spine), and may move the first robotic arm 204 and/or the imaging source 224 closer to the patient. The resulting force applied by the user to move the first robotic arm 204 and/or the imaging source 224 may be captured by the one or more sensors 240 positioned on or within the first robotic arm 204 and/or the imaging source 224, with the resulting sensor data being passed to the computing device 102. The computing device 102 may determine the motion of the first robotic arm 204 and/or the imaging source 224 and determine complementary movement of the second robotic arm 208 and/or the imaging detector 228. In some embodiments, the computing device 102 may cause the second robotic arm 208 and/or the imaging detector 228 to move such that the second distance 340B between the imaging source 224 and the imaging detector 228 is less than the first distance 340A (i.e., the imaging source 224 is closer to the imaging detector 228).

In some embodiments, the first distance 340A and the second distance 340B may be the same or be substantially the same (e.g., within 1% difference, within 2% difference, within 5% difference, etc.). In such embodiments, the user may wish to keep the relative distance between the imaging source 224 and the imaging detector 228 the same but may desire an image of the target anatomical element in a different pose.

Figure 3E:
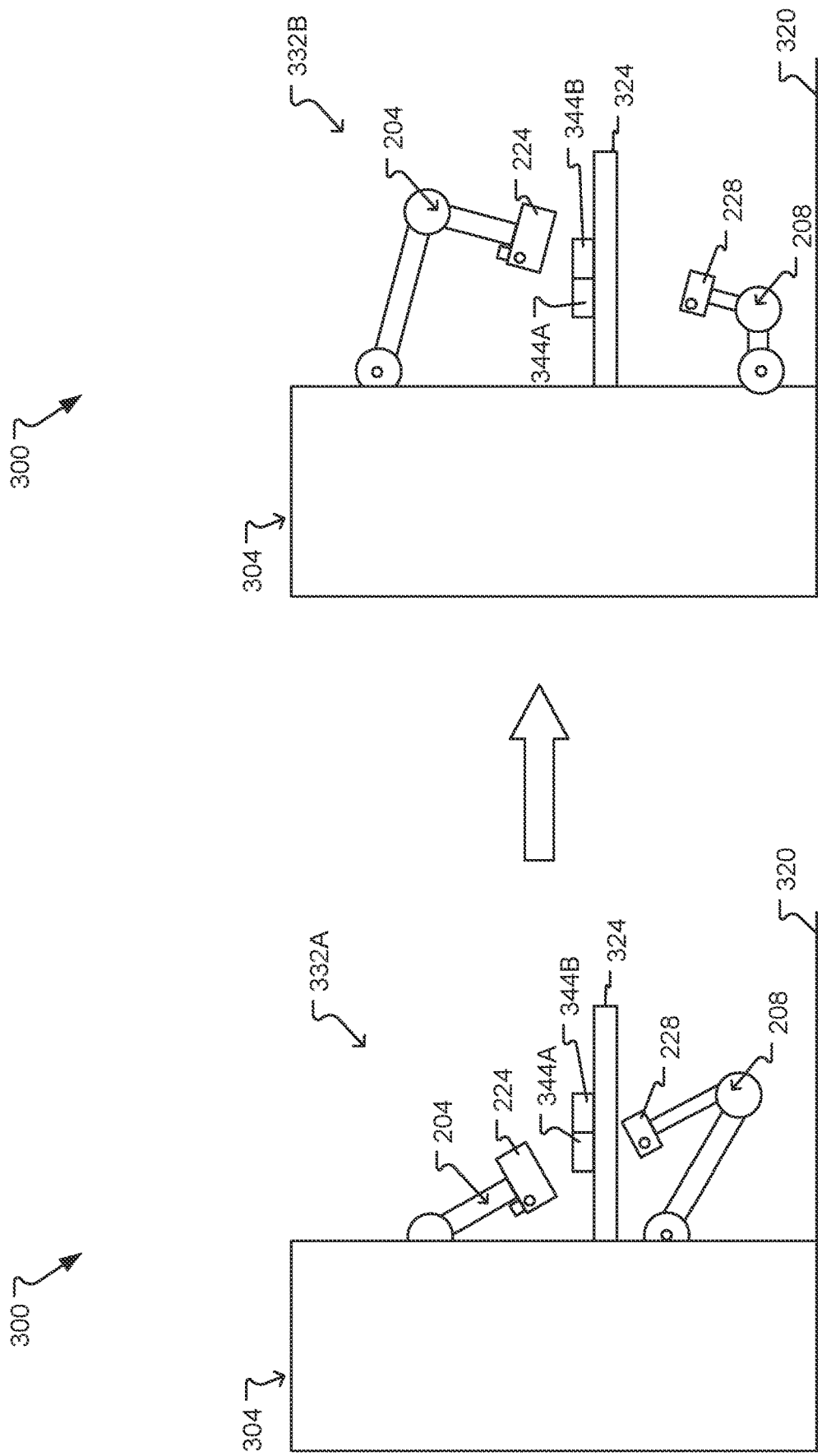
FIG. 3E is a second diagram of the robotic platform according to at least one embodiment of the present disclosure.

In some embodiments, the user may desire to image a different region of interest and may move the first robotic arm 204 from imaging a first region of interest 344A to image a second region of interest 344B. In such embodiments, the robotic arm 208 may then be caused to move in a complementary movement such that images of the second region of interest 344B can be captured. For instance, as shown in FIG. 3E, the regions of interest 344A and 344B may correspond to portions of patient anatomy positioned on the table 324. The surgeon may be imaging one or more cervical vertebrae in the region of interest 344A with the first robotic arm 204 in the first pose 332A and may determine that images of lumbar vertebrae (positioned lower on the patient spine) are required. The surgeon may pull the first robotic arm 204 along a first direction of the table 324, such that the imaging source 224 on the first robotic arm 204 is aligned with the region of interest 344B (which may contain the lumbar vertebrae). The one or more sensors 240 attached to the first robotic arm 204 and/or the imaging source 224 may measure the movement of the first robotic arm 204 and the imaging source 224 and may send the measured data to the computing device 102. The computing device 102 may determine the pose 332B of the first robotic arm 204 and determine a complementary movement of the second robotic arm 208 to align the imaging detector 228 with the imaging source 224, such that images of the region of interest 344B may be captured. Depending on, for example, the type of imaging, the type of surgery, physician preference, or the like, the determined complementary movement of the imaging detector 228 may result in the distance between the imaging source and the imaging detector 228 changing, such that the distance between the imaging detector 228 and the imaging source 224 increases, decreases, or remains substantially the same after the complementary movement of the imaging detector 228.

Figure 3F:
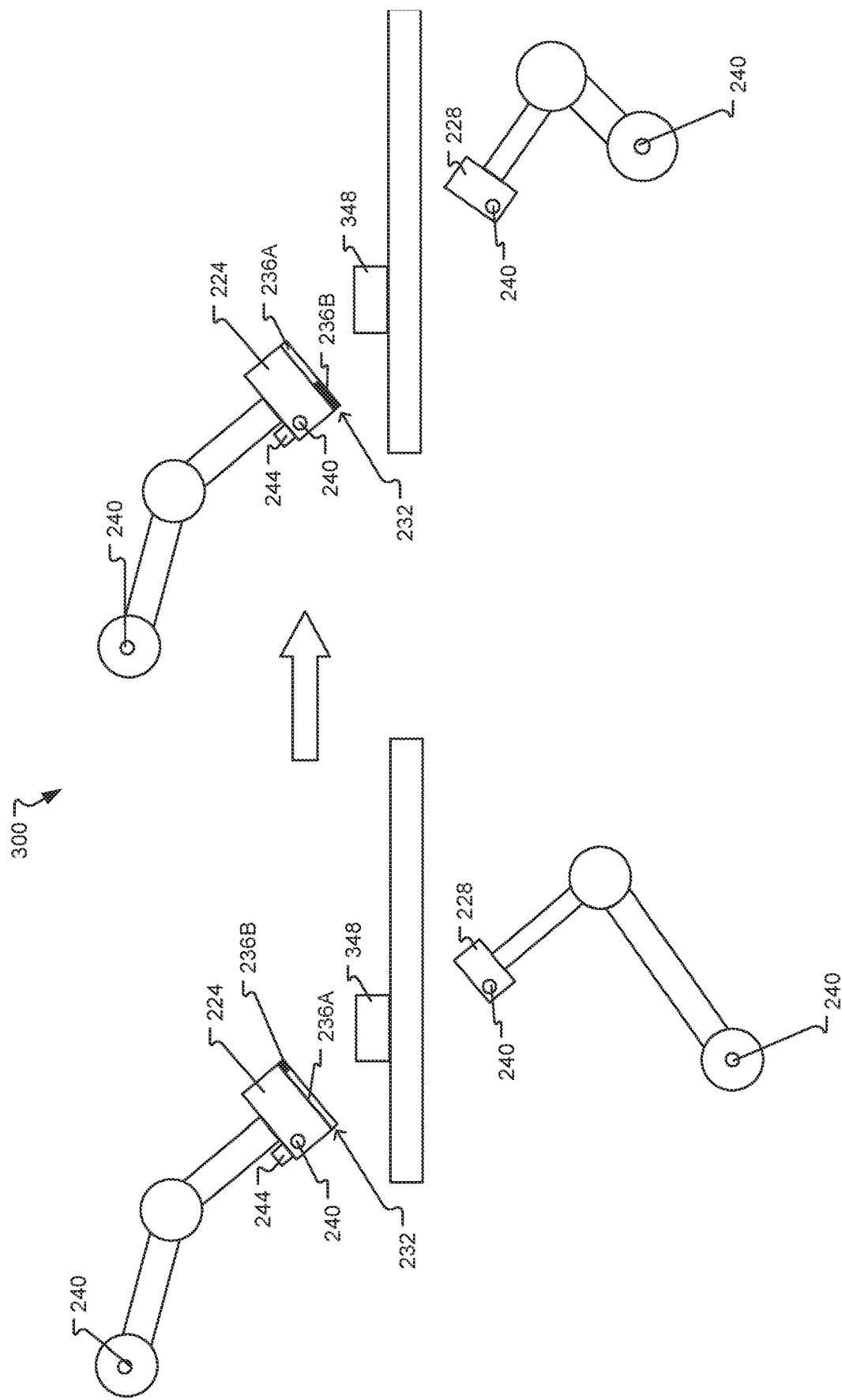
FIG. 3F is a plan view of components of the robotic platform according to at least one embodiment of the present disclosure.

In some embodiments, a collimator 232 may be connected to or coupled with one or more of the imaging source 224 and the imaging detector 228. The collimator 232 may comprise an open portion 236A through which X-rays may pass, as well as a closed portion 236B that prevents the passage of X-rays. As shown in FIG. 3F, the collimator 232 may be adjusted (e.g., using a computing device 102) by changing the dimensions and/or shape of the open portion 236A and the closed portion 236B using, for example, shutters covering the collimator 232 that are connected to the one or more motors 220. In some embodiments, the adjustment of the collimator 232 may occur based on the movement of the first robotic arm 204 and/or the second robotic arm 208. For example, the first robotic arm 204 may be posed such that the open portion 236A of the collimator 232 faces a region of interest 348. The user may then move the second robotic arm 208, such that imaging source 224 and the imaging detector 228 are no longer aligned. The movement of the second robotic arm 208 may trigger the computing device 102 to determine a change of one or more shutters in the collimator 232 to change the areas associated with the open portion 236A and/or the closed portion 236B. The changes may adjust the pose of the collimator 232 such that the X-rays emitted by the imaging source 224 can be captured from by the imaging detector 228. In some embodiments, the changes in the shutters of the collimator 232 may be automatically adjusted based on instructions processed by the computing device 102. In some embodiments, the adjustments to the collimator 232 may occur after the complementary movement of the imaging detector 228, such as when the imaging detector 228 moves, and the resulting images are out of focus, overexposed, or otherwise suboptimal due to an excess or lack of radiation flowing though the collimator 232. For example, the collimator 232 may be adjusted by the computing device 102 based on imaging processing algorithms 120, which may process images captured after the complementary movement of the second robotic arm 208. The image processing algorithms 120 may output information indicating that the captured image is overexposed due to too much radiation (or oppositely underexposed due to a lack of radiation), and the computing device 102 may use the information to cause the open portion 236A to shrink (or oppositely cause the open portion 236A to expand) to improve image quality.

The robotic platform 300 may comprise a locking mechanism 328. The locking mechanism 328 locks and unlocks components of the system 100 and/or the robotic platform 300 (e.g., the robotic arms 116). In some embodiments, the locking mechanism 328 may be or comprise a pedal (e.g., a floor pedal attached to the operating room wall 320) and/or a lever. In some embodiments, the locking mechanism 328 may be utilized by the user to lock or unlock, for example, the movement of the first robotic arm 204 and/or the second robotic arm 208. In one embodiment, the locking mechanism 328 may be a floor pedal that may be pressed by the user when the user wishes to unlock the first robotic arm 204. The floor pedal, once pressed, may cause one or more the one or more members 212A and/or the one or more joints 212B to unlock, such that the members 212A and/or the one or more joints 212B may be capable of moving. In some embodiments, the locking mechanism 328 may unlock specific components or portions of the robotic arms 116, while keeping other components locked. For example, the locking mechanism 328 may cause a joint of the robotic arm 204 directly attached to the support structure 304 to unlock, while keeping the remaining joints in the robotic arm 204 locked, such that the robotic arm 204 can only be rotated but preventing the robotic arm 204 from being translated. In other embodiments, the joint of the robotic arm 204 contacting the support structure 304 may remain locked, while other joints in the robotic arm 204 may become unlocked, such that the robotic arm 204 can be translated, but not rotated.

In some embodiments, the locking mechanism 328 may be push and hold (i.e., the locking mechanism 328 must be continuously held in an "on" state to keep components unlocked) or may alternate between "on" states and "off" states based on user input (e.g., a lever may switch between an "on" state and an "off" state, a button may be "on" when pressed down once and may switch to an "off" state when pressed again). In some embodiments, the locking mechanism 328 may send one or more signals to the computing device 102, which may determine whether to lock or unlock the components of the system 100 and/or the robotic platform 300 based thereon. For instance, the computing device 102 may prevent the components from being moved until a signal from the locking mechanism 328 to unlock the components is received.

The robotic platform 300 or similar systems may be used, for example, to carry out one or more aspects of any of the methods 400 and/or 500 described herein. The robotic platform 300 or similar systems may also be used for other purposes.

Figure 4:
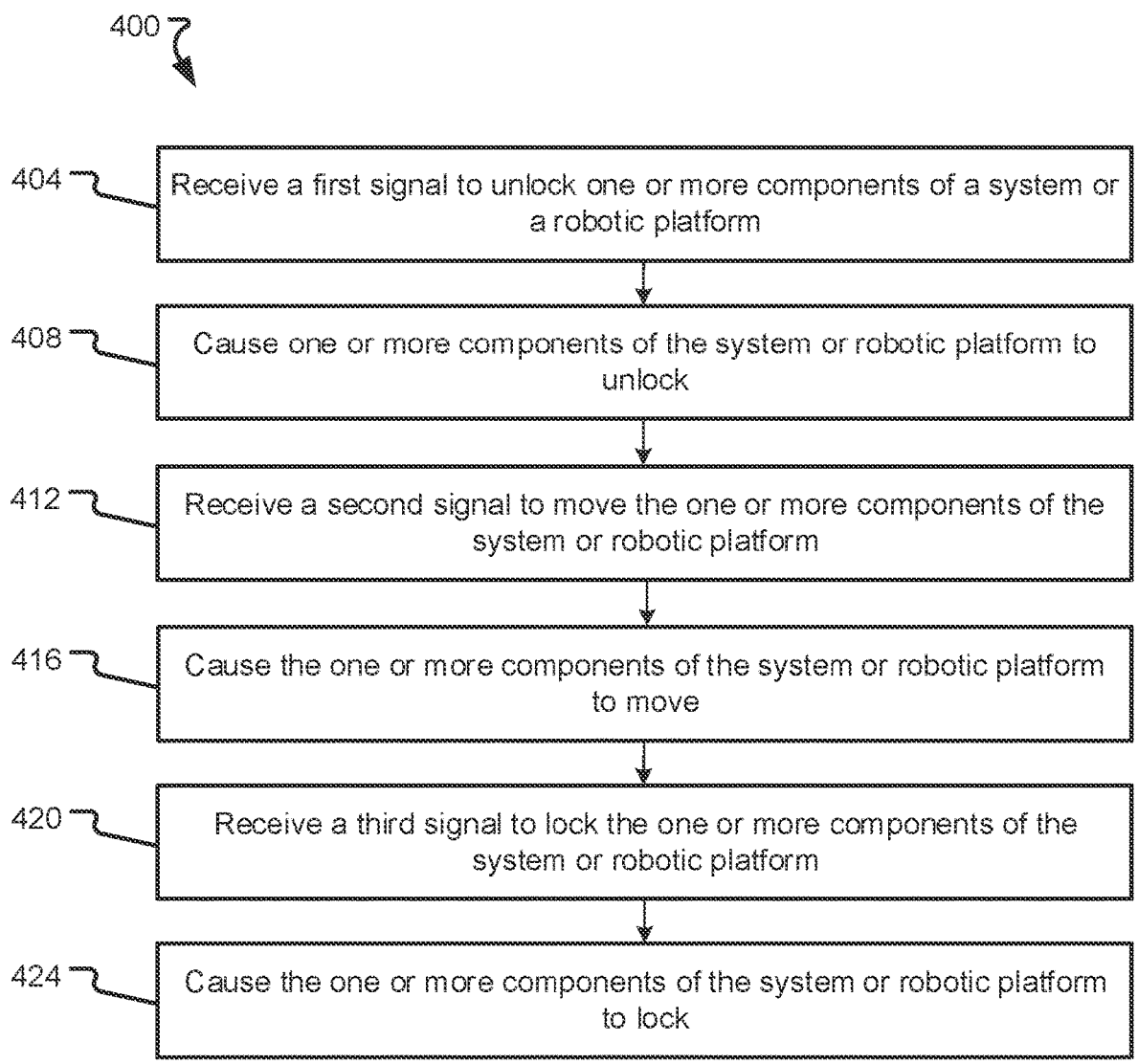
FIG. 4 is a flowchart illustrating a method of manipulating components of a system according to at least one embodiment of the present disclosure.

FIG. 4 depicts a method 400 that may be used, for example, to lock and unlock components of a system or robotic platform to adjust the position of an imaging source and imaging detector.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114), part of robotic arms (such as one or more members 212A, 216A, one or more joints 212B, 216B, an imaging source 224, an imaging detector 228, combinations thereof, or the like), or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a segmentation algorithm 122, a transformation algorithm 124, and/or a registration algorithm 128.

The method 400 comprises receiving a first signal to unlock one or more components of a system or robotic platform (step 404). The first signal may be generated by a locking mechanism (e.g., a locking mechanism 328) that is received by a computing device (e.g., a computing device 102). For instance, the locking mechanism may be a foot pedal on an operating room floor or wall that, when pressed by a user (e.g., a surgeon, a surgical technician, etc.), may send the first signal to the computing device. In some embodiments, the first signal may be sent wirelessly.

The method 400 also comprises causing one or more components of the system or robotic platform to unlock (step 408). The first signal may unlock one or more members (e.g., members 212A, 212B), one or more joints (e.g., joints 216A, 216B), a first and/or second robotic arm (e.g., a first robotic arm 204, a second robotic arm 208, etc.), combinations thereof, or the like. Different components in the system or robotic platform may be unlocked based on, for example, the type of surgery, the number and/or type of components coupled to the locking mechanism, or the like. For example, a first robotic arm may be coupled, linked, or otherwise communicatively connected to the locking mechanism, such that the first signal causes one or more members and/or joints of the robotic arm to unlock.

The method 400 also comprises receiving a second signal to move the one or more components of the system or robotic platform (step 412). The second signal may be generated or sent by one or more sensors (e.g., one or more sensors 240) based on sensor measurements. For instance, the sensor measurements may be directed toward a force applied by the user on a first robotic arm (e.g., a first robotic arm 208) and/or a component connected thereto (e.g., an imaging source 224). In some embodiments, the second signal may be or comprise information relating to the magnitude and/or direction of the measured force, which may indicate that the use wishes to move the first robotic arm. In some embodiments, the second signal may be a collection of signals sent from individual sensors, which may be used by the computing device to determine a total input force (e.g., the user may apply a first force to the first robotic arm, and a second force to the imaging source connected to the first robotic arm).

The method 400 also comprises causing the one or more components of the system or robotic platform to move (step 416). The computing device may determine, based on the second signal, a desired movement and/or pose of the first robotic arm by the user, and cause one or more components of the system or robotic platform to move to the desired pose. For example, the user may wish to move the first robotic arm such that the imaging source is further away from the patient, and the computing device may cause one or more motors to move the one or more members and/or one or more joints of the first robotic arm such that the imaging source moves further away from the patient. In some embodiments, the computing device may cause the one or more components of the system to move based on predetermined instructions. For instance, the robotic platform may be used to capture multiple images of each vertebra of a patient's spine. The resulting reading of the second signal by the computing device may determine that the user has applied a horizontal force on the first robotic arm (e.g., the user pushes the first robotic arm with a force in the same direction as the length of the spine). The computing device may read instructions that cause the computing device to move the one or more components of the system such that the imaging source and a corresponding imaging detector (which may be connected to a second robotic arm) move along the spine and capture images of each vertebra.

The method 400 also comprises receiving a third signal to lock the one or more components of the system or robotic platform (step 420). The third signal may be generated by the locking mechanism and received by the computing device. The third signal may be or comprise information that, when processed by the computing device, causes one or more components of the system or robotic platform to lock. In some embodiments, the locking mechanism may be actuated (e.g., by a user) after the one or more components of the system or robotic platform are moved. For example, the third signal may be generated when the user actuates the locking mechanism (e.g., a floor pedal) after the first robotic arm has been moved and the second robotic arm has been moved in a complementary manner. In some embodiments, the third signal may be sent wirelessly from the locking mechanism to the computing device.

The method 400 also comprises causing the one or more components of the system or robotic platform to lock (step 424). The third signal may cause the one or more members, the one or more joints, the first and/or second robotic arm, combinations thereof, or the like to lock. In some embodiments, the third signal may cause some or all of the components unlocked by the first signal to become locked. For example, the first robotic arm may have been unlocked by the first signal, and the third signal may cause the motors in the first robotic arm to lock, such that the first robotic arm can no longer be moved by the user.

The present disclosure encompasses embodiments of the method 400 that comprise more or fewer steps than those described above, and/or one or more steps that are different than the steps described above.

Figure 5:
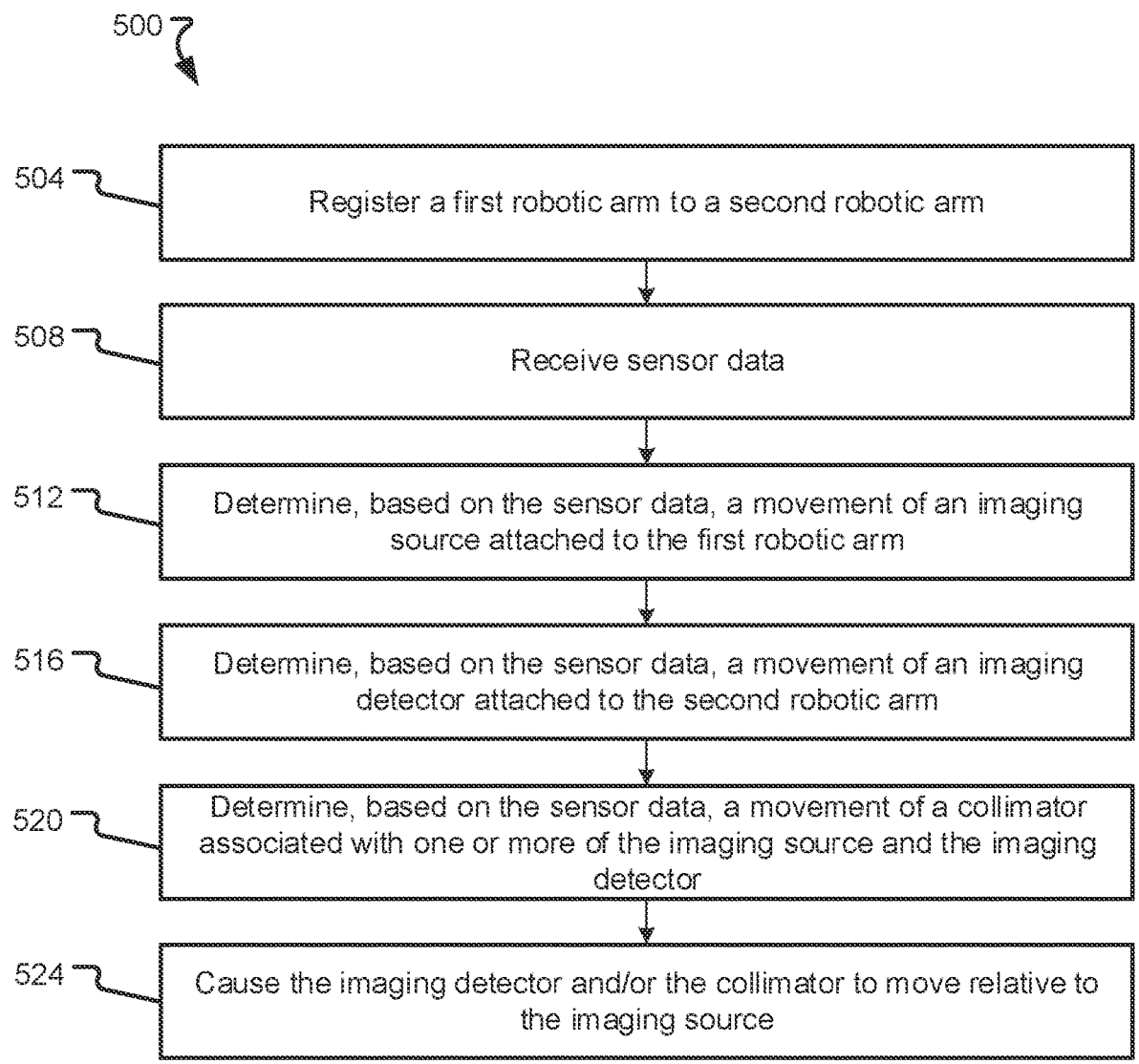
FIG. 5 is a flowchart illustrating a method for controlling imaging components according to at least one embodiment of the present disclosure.

FIG. 5 depicts a method 500 that may be used, for example, to control the pose of a robotic arm (or an imaging detector and/or a collimator attached thereto) based on a pose of another robotic arm (or an imaging source attached thereto).

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114), part of the robotic arms (such as one or more members 212A, 216A, one or more joints 212B, 216B, an imaging source 224, an imaging detector 228, combinations thereof, or the like), or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as an image processing algorithm 120, a segmentation algorithm 122, a transformation algorithm 124, and/or a registration algorithm 128.

The method 500 comprises registering a first robotic arm to a second robotic arm (step 504). A computing device such as the computing device 102 may register the first robotic arm (e.g., a robotic arm 204) and a second robotic arm (e.g., a robotic arm 208) using an algorithm such as a registration algorithm 128. The registering enables for control of the first robotic arm and the second robotic arm in a common coordinate system so as to avoid collisions or undesired contact between the two robotic arms. In some embodiments, one or more portions of the first robotic arm (e.g., an imaging source such as imaging source 224) may be registered with one or more portions of the second robotic arm (e.g., an imaging detector such as imaging detector 228).

The method 500 also comprises receiving sensor data (step 508). The sensor data may be received by one or more sensors (e.g., one or more sensors 240) and may be based on forces or vibrations generated by the user. In some embodiments, the sensor data may be or comprise information related to a magnitude and/or direction of a force applied by the user to, for example, the first robotic arm, the second robotic arm, the collimator, combinations thereof, and/or components thereof (e.g., the one or more members, the one or more joints, etc.).

The method 500 also comprises determining, based on the sensor data, a movement of an imaging source attached to the first robotic arm (step 512). As previously mentioned, the sensor data may be or comprise information related to a magnitude and/or direction of a force applied to the imaging source or a component holding the imaging source, such as the first robotic arm. In some embodiments, the computing device may receive the sensor data and determine the movement of the imaging source. For instance, the computing device may use a transformation algorithm (e.g., a transformation algorithm 124) to receive the force measurements as an input and output a corresponding pose of the imaging source and/or the first robotic arm.

The method 500 also comprises determining, based on the sensor data, a movement of an imaging detector attached to the second robotic arm (step 516). The computing device may make use of the transformation algorithm to determine the required movement of the second robotic arm based on the movement of the imaging source and/or the first robotic arm. For example, the computing device may determine that the imaging source, or similarly the first robotic arm, has been moved from a first pose (e.g., a pose 332A) to a second pose (e.g., a second pose 332B), and may determine a complementary movement for the imaging detector, or the second robotic arm, such that the imaging detector is aligned with the imaging source.

The method 500 also comprises determining, based on the sensor data, a movement of a collimator associated with one or more of the imaging source and the imaging detector (step 520). The computing device may base the movement of the collimator (e.g., a collimator 232) off the determined movement of imaging source and/or the imaging detector, and or the one or more components attached thereto (e.g., the first robotic arm and/or the second robotic arm). For instance, if the collimator is coupled with the second robotic arm, and the first robotic arm moves from the first pose to the second pose, the computing device may determine that an open portion (e.g., an open portion 236A) of the collimator should be repositioned or changed to allow for complementary alignment of the imaging source and imaging detector. Additionally or alternatively, the computing device may cause the pose of the open portion and a closed portion (e.g., a closed portion 236B) of the collimator to stay the same, but instead cause the imaging detector to which the collimator is connected to change in pose to allow for the complementary alignment with the imaging source.

The method 500 also comprises causing the imaging detector and/or the collimator to move relative to the imaging source (step 524). The computing device may output a control signal to one or more components of the system or robotic platform (e.g., to the robotic arms, or the members and/or joints thereof) to cause the one or more components to move based on the determinations made by the computing device. In some embodiments, the movement of the imaging detector and/or collimator may be done substantially synchronously. In other embodiments, the computing device may output control signals to cause such movement, but may require user input (e.g., the user may need to activate or actuate the locking mechanism again) before outputting the control signals to cause the components of the system to move. In some embodiments, the imaging source and/or collimator may be caused to move relative to the imaging detector. In such embodiments, the sensor data may indicate and the computing device may determine that the second robotic arm is being moved (e.g., by the user), and may determine a complementary movement of the imaging source and cause the imaging source to move in such a manner (e.g., by controlling movement of the first robotic arm).

The present disclosure encompasses embodiments of the method 500 that comprise more or fewer steps than those described above, and/or one or more steps that are different than the steps described above.

As noted above, the present disclosure encompasses methods with fewer than all of the steps identified in FIGS. 4 and 5 (and the corresponding description of the methods 400 and 500), as well as methods that include additional steps beyond those identified in FIGS. 4 and 5 (and the corresponding description of the methods 400 and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system, comprising:
    an imaging source;
    an imaging detector spaced a first distance from the imaging source when the imaging source is in a first orientation;
    a sensor coupled to at least one of the imaging source and the imaging detector; and
    a controller that adjusts a relative position of the imaging source and the imaging detector based on an output of the sensor, wherein the controller moves the imaging detector to a second distance from the imaging source when the imaging source moves into a second orientation, and wherein the second distance is different from the first distance.

2. The system of claim 1, wherein the sensor comprises a force sensor.

3. The system of claim 1, wherein the imaging source is moved with a first robotic arm, and wherein the imaging detector is moved with a second robotic arm.

4. The system of claim 1, wherein the controller adjusts at least one of the imaging source and the imaging detector using an electromechanical linkage, and wherein the electromechanical linkage comprises an O-arm, a C-arm, or a G-arm.

5. The system of claim 1, wherein the controller adjusts the relative position of the imaging source and the imaging detector such that the imaging source is substantially aligned with the imaging detector.

6. The system of claim 1, wherein the first distance is greater than the second distance.

7. The system of claim 1, wherein the first distance is less than the second distance.

8. The system of claim 1, further comprising:
    a collimator operatively coupled with at least one of the imaging source and the imaging detector, the collimator including an open portion and a closed portion, wherein the controller adjusts a position of at least one of the open portion and the closed portion of the collimator based on the output of the sensor.

9. The system of claim 8, wherein the controller adjusts the position of the at least one of the open portion and the closed portion of the collimator relative to the imaging source such that the collimator is aligned with the imaging source along a first axis.

10. A system comprising:
a first robotic arm connected to an imaging source in a first orientation;
a second robotic arm connected to an imaging detector, the imaging detector spaced a first distance from the imaging source when the imaging source is in the first orientation;
a sensor operatively coupled with the first robotic arm; and
a controller that receives a first input from the sensor related to a movement of the first robotic arm to position the imaging source in a second orientation, wherein the controller causes the second robotic arm to move relative to the first robotic arm such that the imaging detector is spaced a second distance from the imaging source once the imaging detector moves.

11. The system of claim 10, wherein the sensor comprises a force sensor.

12. The system of claim 10, further comprising:
a locking mechanism that switches one or more of the first robotic arm and the second robotic arm between a locked state and an unlocked state, wherein, when in the locked state, the first robotic arm and the second robotic arm are prevented from being moved, and wherein, when in the unlocked state, the first robotic arm and the second robotic arm are configured to be moved.

13. The system of claim 12, wherein the locking mechanism comprises at least one of a floor pedal, a button, and a lever.

14. The system of claim 10, further comprising:
a collimator operatively connected to at least one of the imaging source and the imaging detector, the collimator including an open portion and a closed portion, wherein at least one of the open portion and the closed portion of the collimator is configured to be adjusted based on an output of the sensor.

15. The system of claim 14, wherein the open portion and the closed portion of the collimator are in a third orientation at a first time, and wherein, at a second time, the controller moves the collimator into a fourth orientation different from the third orientation by adjusting the at least one of the open portion and the closed portion of the collimator.

16. The system of claim 15, wherein the collimator is substantially aligned with the imaging source in at least one of the third orientation and the fourth orientation.

17. A system, comprising:
a processor; and
a memory storing data for processing by the processor that, when processed by the processor, cause the processor to:
receive an input from at least one sensor, the input related to a movement of a first robotic arm to reposition an imaging source from a first orientation to a second orientation; and
output a control signal, the control signal causing a second robotic arm to move relative to the first robotic arm such that an imaging detector connected to the second robotic arm and initially a first distance from the first robotic arm moves, wherein the imaging detector is a second distance from the imaging source different from the first distance after the second robotic arm moves relative to the first robotic arm.

18. The system of claim 17, wherein the second robotic arm moves substantially synchronously with the first robotic arm.

19. The system of claim 17, further comprising a collimator with an open portion and a closed portion, wherein the data, when processed by the processor, further cause the processor to:
adjust, based on the control signal, at least one of the open portion and the closed portion of the collimator.

20. The system of claim 19, wherein the collimator is substantially aligned with the imaging source in at least one of the first orientation and the second orientation.

* * * * *